United States Patent [19]

Eastman et al.

[11] Patent Number: 4,956,476

[45] Date of Patent: Sep. 11, 1990

[54] PREPARATION OF THIOLACTAMS

[75] Inventors: Alan D. Eastman; Marvin M. Johnson; Richard D. Skinner, all of Bartlesville, Okla.

[73] Assignee: Phillips Petroleum Company, Bartlesville, Okla.

[21] Appl. No.: 486,709

[22] Filed: Mar. 1, 1990

[51] Int. Cl.$^5$ ............... C07D 201/02; C07D 207/267; C07D 211/76; C07D 223/02

[52] U.S. Cl. .................................... 548/552; 540/538; 546/243

[58] Field of Search ............... 548/543, 552; 540/538; 546/243

[56] References Cited

U.S. PATENT DOCUMENTS 3,306,910 2/1967 Louthan .................. 260/326.83
3,397,210 8/1968 Michalowicz ................ 548/548
4,145,352 3/1979 Kubiuk .................... 260/326.82

Primary Examiner—David B. Springer
Attorney, Agent, or Firm—K. K. Brandes

[57] ABSTRACT

The reaction of lactams (preferably N-methyl-2-pyrrolidone) with hydrogen sulfide to thiolactams (preferably N-methyl-2-thiopyrrolidone) is conducted in the presence of a catalyst consisting essentially of alumina.

15 Claims, No Drawings

PREPARATION OF THIOLACTAMS

BACKGROUND OF THE INVENTION

This invention relates to the catalytic conversion of hydrogen sulfide and lactams (cyclic amides) to thiolactams. In a particular aspect, this invention relates to the catalytic reaction of N-methyl-2-pyrrolidone with hydrogen sulfide to N-methyl-2-thiopyrrolidone (also referred to as N-methylpyrrolidine-2-thione).

The catalytic conversion of lactams (in particular N-methyl-2-pyrrolidone) and $H_2S$ to thiolactams (in particular N-methyl-2-thiopyrrolidone) is known and has been described in U.S. Pat. No. 4,145,352, the entire disclosure of which is incorporated herein by reference. As has been pointed out in this patent, N-methyl-2-thiopyrrolidone can be used as a sulfur source in the preparation of poly(phenylene sulfide). The instant invention is directed to an improvement of the process of U.S. Pat. No. 4,145,352 by employing a more effective catalyst.

SUMMARY OF THE INVENTION

It is an object to prepare this lactams by the catalytic reaction of lactams with hydrogen sulfide. It is another object of this invention to prepare N-methyl-2-thiopyrrolidone from N-methyl-2-pyrrolidone and $H_2S$. Other objects and advantages will become apparent from the detailed disclosure and the appended claims.

In accordance with this invention, in a process for reacting at least one lactam with hydrogen sulfide so as to produce at least one thiolactam, the improvement comprises employing a catalyst consisting essentially of alumina.

DETAILED DESCRIPTION OF THE INVENTION

Any suitable lactam (cyclic amide) can be employed as reactant in the process of this invention. These lactams are represented by the structural formula:

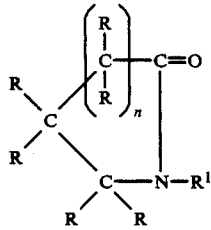

wherein each R and $R^1$ is independently selected from the group consisting of hydrogen, alkyl radicals and cycloalkyl radicals, and combinations thereof, preferably containing from 1 to 6 carbon atoms; and n can be an integer in the range of from 0 to 10. The total number of carbon atoms in these lactams generally should not exceed 20.

Lactams which can be converted to thiolactams by the process of this invention include 2-azetidinone, 2-pyrrolidone, 2-piperidone, 2-oxohexamethylenimine(-caprolactam), N-methyl-2-azetidinone, N-methyl-2-pyrrolidone, N-ethyl-2-pyrrolidone, N-propyl-2-pyrrolidone, 2-oxo-1-ethylhexamethylenimine, 3,3-di-n-propyl-2-piperidone, 2-oxo-4-n-hexyl-hexamethylenimine, 2-oxo-2-cyclopentylhexamethylenimine, lactam of 7-(cyclohexylamino)-heptanoic acid, lactam of 13-aminotridecanoic acid, 3,4,5-tri-n-pentyl-2-piperidone, 3-cyclopentyl-2-pyrrolidone, lactam of 3-amino-3-cyclohexyl-4-ethyloctanoic acid, 1-isopropyl-2-pyrrolidone, 2-oxo-1-ethyl-3-tert-butylhexamethylenimine, and the like. Preferred lactams are N-alkyl-2-pyrrolidones with the alkyl group containing 1-3 carbon atoms; in particular N-methyl-2-pyrrolidone.

The thiolactams which are prepared by this invention are represented by the formula:

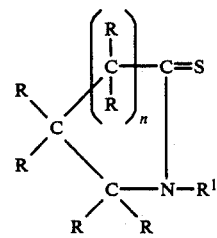

wherein R, R' and n are as defined above (for lactams).

The preferred thiolactams are N-alkyl-2-thiopyrrolidones with the alkyl group containing 1-3 carbon atoms, in particular N-methyl-2-thiopyrrolidone.

The catalyst which is employed in the process of this invention consists essentially of alumina. Any suitable alumina material (many of which are commercially available) can be employed as catalyst. The method of preparation of alumina is not considered critical. Generally, first hydroxides and/or hydrated oxides of aluminum are precipitated from an aqueous solution of a dissolved aluminum compound by means of a suitable alkaline substance (e.g., aqueous $NH_3$). Then the precipitate is separated, washed, and finally heated (calcined) so as to remove water therefrom and to convert the hydroxide to an oxide of aluminum, preferably chi-alumina or eta-alumina or gamma-alumina or combinations thereof.

The surface area (determined by the BET method employing $N_2$; substantially in accordance with ASTM D3037) of alumina should exceed about 10 $m^2/g$, and generally is in the range of from about 10 to about 400 $m^2/g$. The alumina particles can have spherical, trilobal, quadrilobal or irregular shape. Impurities should be substantially absent from the support material (i.e., they should not be present at a level higher than about 0.5, preferably less than about 0.2 weight-%). Preferred alumina materials which are used as catalysts in the process of this invention are described in the Examples.

The reaction conditions for the catalyzed preparation of thiolactams described herein are considered to be mild. Generally, the reaction is carried out at an elevated temperature of about 500°–800° F., with a preferred range of about 500° to about 700° F. (about 260°–371° C.). The reaction can be carried out at a pressure ranging from about 1 to about 1000 psia, with a preferred pressure range of about 7 to about 150 psia (about 0.5–10 atm).

Although the invention is operable over a broad range of molar ratios of the reactants and with a broad range of feed rates, the usual range of the molar ratio of $H_2S$ to lactam in the feed is about 2:1 to about 20:1, with a preferred range of about 3:1 to about 12:1. It is understood that $H_2S$ and lactam can be introduced simultaneously but separately into the reaction zone, or they can be introduced together in one feed stream. The weight hourly space velocity of the lactam will generally be in the range of from about 1 to about 2000 g lactam/g catalyst/hour, preferably about 2–200 g/g/hour.

The formed thiolactam can be separated from unconverted reactants (lactam and $H_2S$) and from by-products, such as water (which is also formed in the reaction), by any suitable separating means, such as fractional distillation, and can then be recovered. Unconverted lactam and $H_2S$ can be recycled to the reaction zone. The reaction of this invention and the subsequent separation steps can be carried out as batch operations or continuously (the latter being preferred).

The following example is presented in further illustration of the invention and are not to be considered as unduly limiting the scope of this invention.

EXAMPLE

This example illustrates the reaction of N-methyl-2-pyrrolidone (NMP) with $H_2S$ to N-methyl-2-thiopyrrolidone (TNMP) and water, in the presence of alumina-containing catalysts.

A tubular stainless steel reactor of 80 cc internal volume was charged with a support layer of inert α-alumina (Alundume ®; surface area: about 1 $m^2/g$), a layer of 10 cc of a catalyst, and a top layer of Alundum ®. The reactor was heated to the desired reaction temperature by means of three-zone electrical furnace. $H_2S$ gas was introduced through an inlet tube at the reactor top, generally at a gas hourly space velocity (GHSV) of about 1,800–2,500 cc $H_2S$ per cc catalyst. Liquid NMP was introduced through another inlet tube at the reactor top, generally at a weight hourly space velocity of about 3–10 g NMP per g catalyst per hour. The gaseous effluent was analyzed by means of a gas chromatograph.

Three catalysts were tested:

(A) Catapal D alumina, a gamma-alumina provided by Vista Chemical Company (Houston, Tex.) having a surface area of about 270 $m^2/g$ (determined by the BET method employing $N_2$) and a pore volume of about 0.70 cc/g; containing 99.8 weight-% alumina and about 0.2 weight-% $TiO_2$, (B) S-201 alumina, a gamma-alumina provided by Kaiser Aluminum Company (Los Angeles, Calif.) having a BET/$N_2$ surface area of 325 $m^2/g$ and a pore volume of 0.40 cc/g, and (C) a catalyst in accordance with U.S. Pat. No. 4,145,352 comprising 5 weight-% phosphotungstic acid on alumina.

Reaction conditions and test results are summarized below:

sisting essentially of alumina versus the catalyst of U.S. Pat. No. 4,145,352 (phosphotungstic acid on alumina).

Reasonable variations and modifications are possible within the scope of the disclosure of this invention and the appended claims.

That which is claimed is:

1. In a process for catalytically reacting at least one lactam with hydrogen sulfide so as to produce at least one thiolactam, the improvement which comprises employing a catalyst consisting essentially of alumina.

2. A process in accordance with claim 1, wherein said alumina is selected from the group consisting of chi-alumina, eta-alumina, gamma-alumina, and combinations thereof.

3. A process in accordance with claim 2, wherein said alumina has a surface area, determined by the BET method employing $N_2$, in excess of about 10 $m^2/g$.

4. A process in accordance with claim 3, wherein said surface area is about 10–400 $m^2/g$.

5. A process in accordance with claim 1, wherein said at least one lactam is a N-alkyl-2-pyrrolidone with the alkyl group containing 1–3 carbon atoms, and the thiolactam is a N-alkyl-2-thiopyrrolidone with the alkyl group containing 1–3 carbon atoms.

6. A process in accordance with claim 1, wherein said process is carried out at a temperature of about 500°–800° F. and a molar ratio of $H_2S$ to lactam of about 2:1 to about 20:1.

7. In a process for reacting N-methyl-2-pyrrolidone with hydrogen sulfide so as to produce N-methyl-2-thiopyrrolidone, the improvement which comprises employing a catalyst consisting essentially of alumina.

8. A process in accordance with claim 7, wherein said alumina is selected from the group consisting of chi-alumina, eta-alumina, gamma-alumina, and combinations thereof.

9. A process in accordance with claim 8, wherein said alumina has a surface area, determined in accordance with the BET method employing $N_2$, exceeds about 10 $m^2/g$.

10. A process in accordance with claim 9, wherein said surface area is about 10–400 $m^2/g$.

11. A process in accordance with claim 7, wherein said process is carried out at about 500°–800° .F and a molar ratio of $H_2S$ to N-methyl-2-pyrrolidone of about 2:1 to about 20:1.

12. A process in accordance with claim 7, wherein said temperature is about 600°–750° F. and said molar ratio is about 3:1 to about 12:1.

13. A process in accordance with claim 7, wherein the weight hourly space velocity of N-methyl-2-pyrroli-

TABLE

| Catalyst | Average Reaction Temp. (°F.) | Average Pressure (psia) | Average GHSV of $H_2S$ | Average Molar Ratio of $H_2S$/NMP | Average Conversion of NMP (%) | Average Selectivity to TNMP (%)[5] |
|---|---|---|---|---|---|---|
| A[1] (Invention) | 666 | 16.0 | 2290 | 8.2:1 | 26.4 | 99.5 |
| A[2] (Invention) | 625 | 15.3 | 2350 | 8.1:1 | 26.0 | 100 |
| B[3] (Invention) | 725 | 15.0 | 2150 | 5.6:1 | 26.4 | 96.0 |
| C[4] (Control) | 725 | 17.1 | 2070 | 5.0:1 | 7.8 | 79.2 |

[1] average of 22 measurements during 488 hours on stream
[2] average of 27 measurements during 359 hours on stream
[3] average of 42 measurements during 351 hours on stream
[4] average of 5 measurements during 43 hours on stream
[5] calculated on a water-free basis The test results in the table clearly show the unexpected superiority of the two invention catalysts condone is about 1 to about 2,000 g per gram catalyst per hour.

14. A process in accordance with claim 7, wherein said process is carried out at a pressure of about 1 to about 1,000 psia.

15. A process in accordance with claim 7, wherein said N-methyl-2-thiopyrrolidone is recovered after having been separated from unconverted N-methyl-2-pyrrolidone and H$_2$S and from formed water.

* * * * *